United States Patent
Lee et al.

(10) Patent No.: US 12,414,959 B2
(45) Date of Patent: Sep. 16, 2025

(54) GLUCOSE INFUSION SOLUTION COMPOSITION

(71) Applicants: Geon Moo Lee, Gwangju (KR); In Seong Lee, Gwangju (KR); Jun Seong Lee, Gwangju (KR); Mi Boon Chung, Seoul (KR); Jin Kyu Song, Gwangju (KR)

(72) Inventors: Geon Moo Lee, Gwangju (KR); In Seong Lee, Gwangju (KR); Jun Seong Lee, Gwangju (KR); Mi Boon Chung, Seoul (KR); Jin Kyu Song, Gwangju (KR)

( * ) Notice: Subject to any disclaimer, the term of this patent is extended or adjusted under 35 U.S.C. 154(b) by 0 days.

(21) Appl. No.: 17/506,227

(22) Filed: Oct. 20, 2021

(65) Prior Publication Data

US 2022/0031718 A1     Feb. 3, 2022

Related U.S. Application Data

(63) Continuation of application No. 16/493,004, filed as application No. PCT/KR2018/002918 on Mar. 13, 2018, now abandoned.

(30) Foreign Application Priority Data

Mar. 15, 2017    (KR) ........................ 10-2017-0032477

(51) Int. Cl.
| | |
|---|---|
| *A61K 31/7004* | (2006.01) |
| *A61K 9/08* | (2006.01) |
| *A61K 31/7008* | (2006.01) |
| *A61K 47/18* | (2017.01) |

(52) U.S. Cl.
CPC ............ *A61K 31/7004* (2013.01); *A61K 9/08* (2013.01); *A61K 31/7008* (2013.01); *A61K 47/183* (2013.01)

(58) Field of Classification Search
None
See application file for complete search history.

(56) References Cited

U.S. PATENT DOCUMENTS

| | | |
|---|---|---|
| 4,670,261 A | 6/1987 | Samejima et al. |
| 6,812,222 B1 | 11/2004 | Wu et al. |
| 2002/0150666 A1 | 10/2002 | Kampinga et al. |
| 2016/0022713 A1 | 1/2016 | Wang |
| 2020/0188686 A1 | 6/2020 | Kalmeta |

FOREIGN PATENT DOCUMENTS

| | | |
|---|---|---|
| CN | 85107296 A | 4/1987 |
| CN | 103284156 A | 9/2013 |
| KR | 10-1989-0002948 | 8/1989 |
| KR | 10-2011-0087614 A | 8/2011 |
| KR | 10-1672347 B1 | 11/2016 |
| WO | WO-2015/200027 A1 | 12/2015 |

OTHER PUBLICATIONS

International Search Report from corresponding PCT Application No. PCT/KR2018/002918, mailed on Jun. 11, 2018.
Extended European Search Report from corresponding European Patent Application No. 18768107.7, dated Aug. 13, 2020.
Office Action (Non-Final) from corresponding U.S. Appl. No. 16/493,004, dated Sep. 16, 2020.
Office Action (Final) from corresponding U.S. Appl. No. 16/493,004, dated Apr. 21, 2021.
Lee, M. H., Lin, Y. S., Tu, C. F., & Yen, C.H. (2014). Recombinant human factor IX produced from transgenic porcine milk. BioMed research international, 2014. (Year: 2014).
Wu, G., & Knabe, D. A. (1994). Free and protein-bound amino acids in saw's colostrum and milk. The Journal of nutrition, 124(3), 415-424. (Year: 1994).
Bell, F. R., & McLeay, L. M. (1978). The effect of duodenal infusion of milk, casein, lactose and fat on gastric emptying and acid secretion in the milk-fed calf. The Journal of Physiology, 282(1), 51-57. (Year: 1978).
Increased Thermal Stability of Proteins in the Presence of Sugars and Polyols; Joan F. Back et al., Biochemistry, vol. 18, No. 23, pp. 5191~5196 (Nov. 13, 1979).
"Food Chemical principle", Chen, Xiangyun et al., p. 145, University Press of South Chinese Technology, Feb. 28, 2015.

*Primary Examiner* — Dale R Miller
(74) *Attorney, Agent, or Firm* — Harness, Dickey & Pierce, P.L.C.

(57) ABSTRACT

An infusion solution composition having enhanced stability is disclosed.

2 Claims, 4 Drawing Sheets

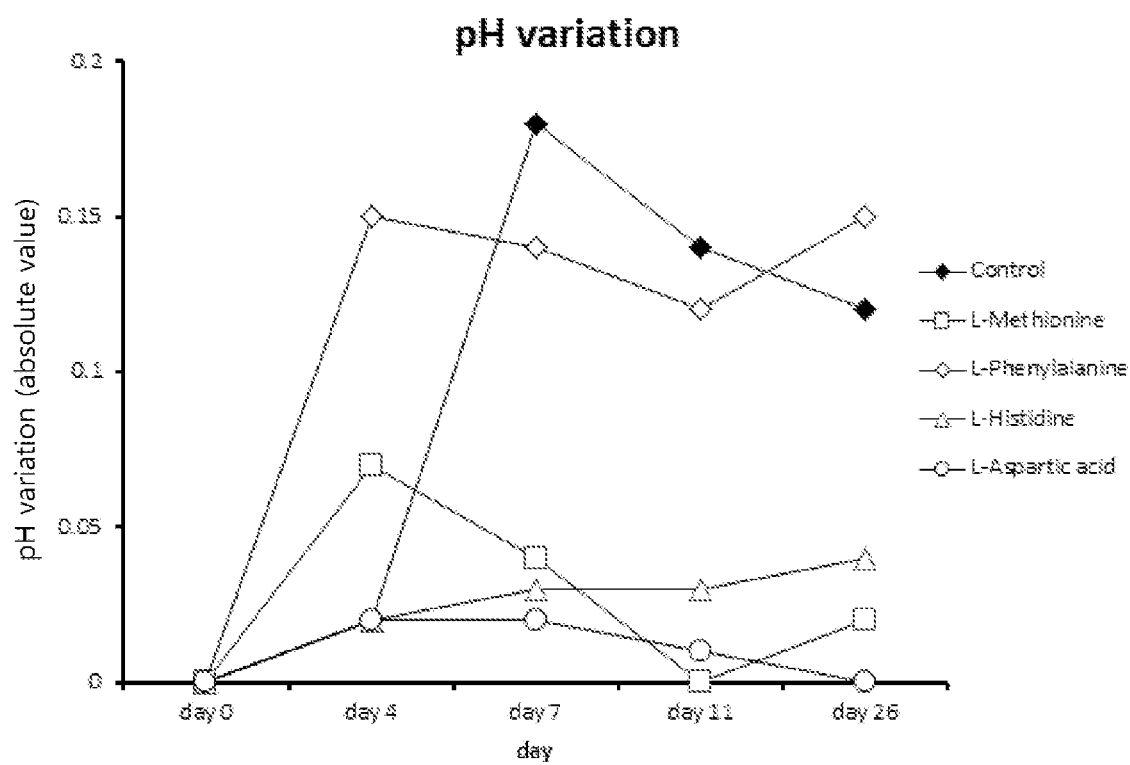
Fig. 1. pH variation caused by the addition of amino acids.

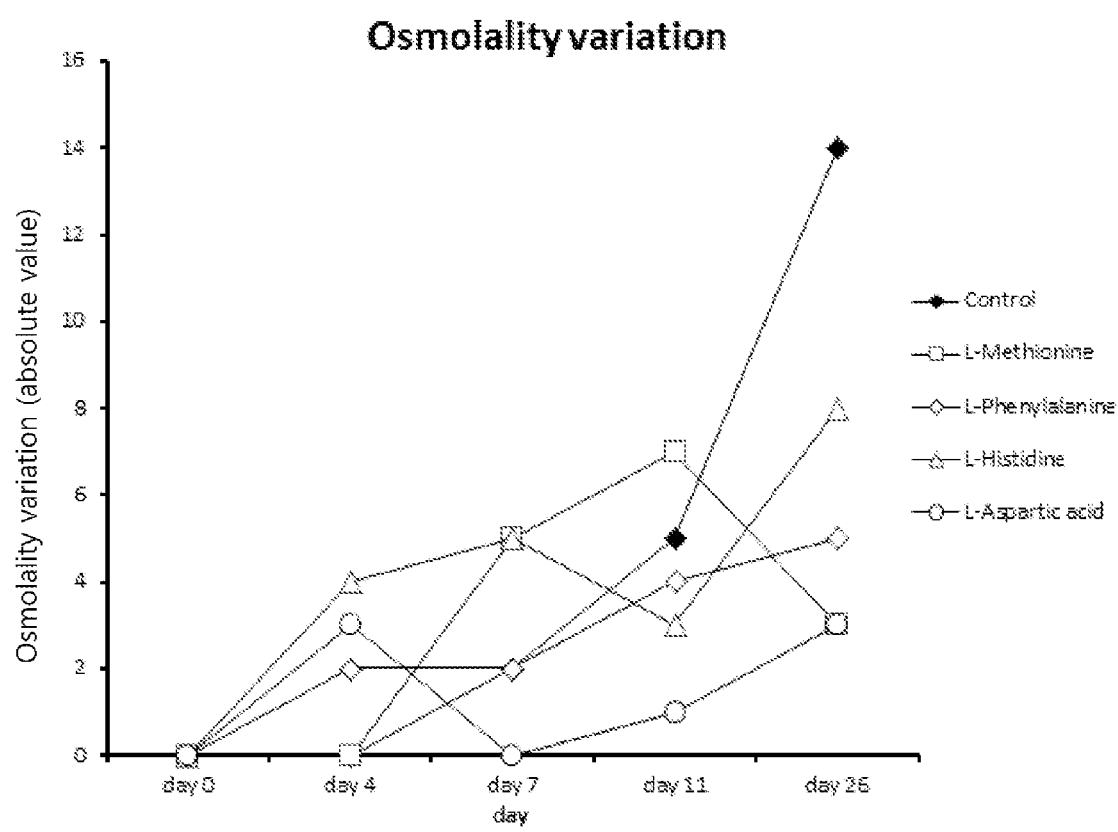
Fig. 2. Osmolality variation caused by the addition of amino acids.

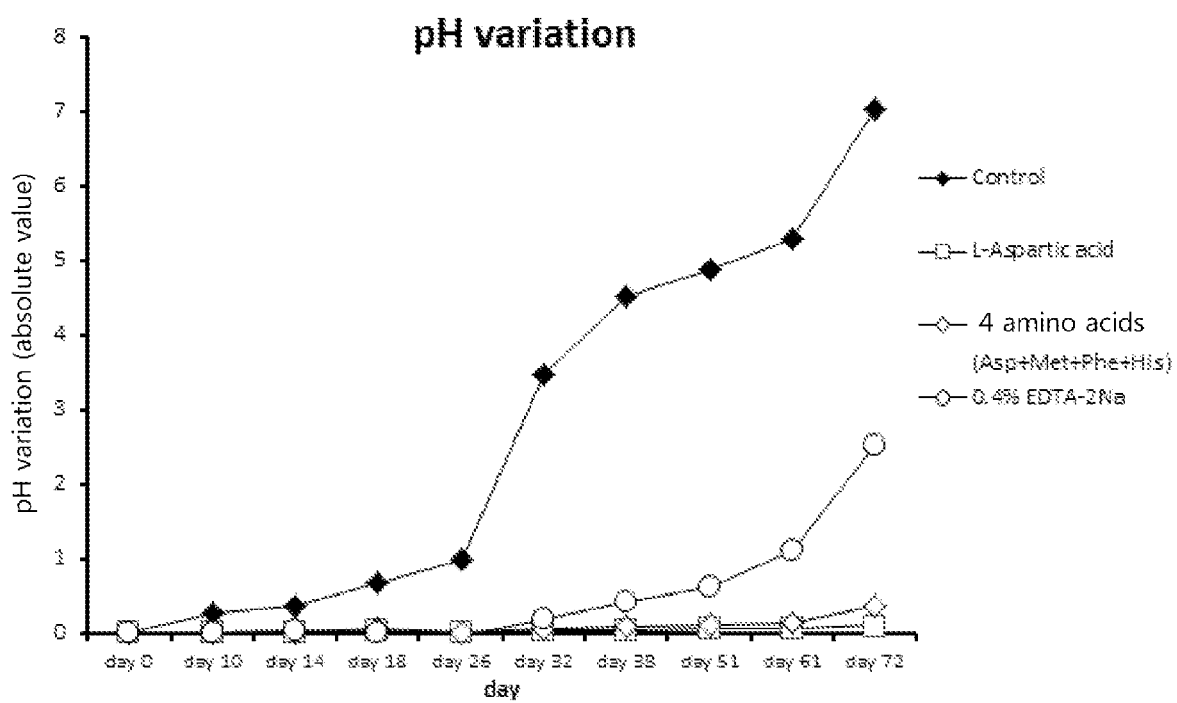
Fig. 3. pH variation caused by the addition of amino acids and EDTA-2Na dihydrate.

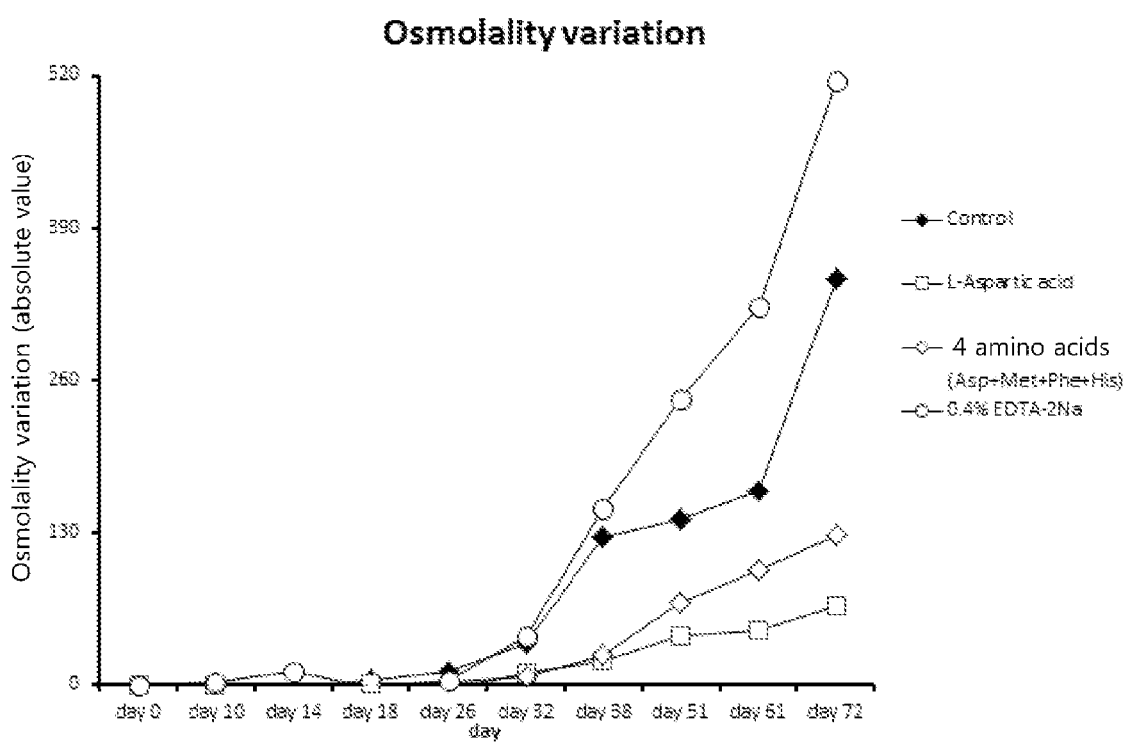
Fig. 4 Osmolality variation caused by the addition of amino acids and EDTA-2Na dihydrate.

GLUCOSE INFUSION SOLUTION COMPOSITION

CROSS-REFERENCE TO RELATED APPLICATIONS

This application is a continuation application of U.S. application Ser. No. 16/493,004, filed on Sep. 11, 2019, which is a national phase application of PCT Application No. PCT/KR2018/002918, filed on Mar. 13, 2018, which claims benefit of Korean Patent Application 10-2017-0032477, filed on Mar. 15, 2017. The entire disclosure of the applications identified in this paragraph is incorporated herein by references.

FIELD

The present invention relates to a sugar infusion solution composition. The sugar infusion solution composition according to the present invention enhances the immune system, promotes health, and particularly, has improved stability.

BACKGROUND

The major substances covered in the life sciences are proteins, amino acids, nucleic acids, fats, fatty acids, carbohydrates, polysaccharides and sugars, etc. Life science and medical researchers have long been engaged in research, understanding that proteins are the main communication molecules in vivo, but have concluded that proteins are not enough to deliver all the messages into cells. As a result, it has been found that carbohydrates such as sugars play an important role in health beneficial body structures and functional harmonization by being involved in immune system regulation, hormone secretion, and major signaling processes in vivo, in addition to producing energy. Therefore, studies have begun on glycoproteins consisting of protein and carbohydrate molecules. Among them, some sugar molecules, in particular, have been found to play an indispensable role in maintaining homeostasis in the human body, but these molecules are sometimes not smoothly supplied in necessary amounts only by food intake. Therefore, it is necessary to supply specific sugars to maintain the health of the human body. In particular, eight sugars, including glucose (Glu), galactose (Gal), mannose (Man), L-fucose (Fuc), xylose (Xy), N-acetylglucosamine (GlcNAc), N-acetylgalactosamine (GalNAc), and N-acetylneuraminic acid (NANA, also known as sialic acid), play a very important role in maintaining physiological activity in the body, and thus supplying them as necessary is very important for maintaining human health.

Sugars can be absorbed rapidly and reliably, particularly when supplied as infusion solutions. However, when sugars are dissolved in water, the stability thereof is generally greatly impaired not only by light and oxygen, but also by water. The present inventors have conducted studies to prevent this impairment, and as a result, have discovered substances that can improve the stability of infusion solution more strongly than conventional stabilizers that maintain the stability of infusion solution, when supplying specific sugar components as infusion solution. The present invention provides the type of stabilizer capable of significantly improving the stability of a specific sugar aqueous solution that may be used as infusion solution, and also provides a sugar infusion solution having improved stability.

SUMMARY

Technical Problem

The present invention is intended to provide a sugar infusion solution having excellent stability.

Technical Solution

To solve the above problem, the present invention discloses a sugar infusion solution having improved effectiveness and stability by comprising specific sugars and specific amino acids.

Advantageous Effects

The sugar infusion solution according to the present invention, when infused into the body, can enhance the immune system and promote health. In particular, infusion solution is not used immediately after preparation, but is generally used while being stored for usually 12 to 24 months in a hospital or clinic. In addition, when the maximum expiration date is assumed to be 24 months, storage stability is a very important factor to be considered in the preparation of infusion solution. Thus, the infusion solution composition according to the present invention has very greatly improved stability.

BRIEF DESCRIPTION OF THE DRAWINGS

FIG. 1 shows the pH variation of sugar solution caused by the addition of specific amino acids as stabilizers.

FIG. 2 shows the osmolality variation of sugar solution caused by the addition of specific amino acids as stabilizers.

FIG. 3 shows the pH variation of sugar solution caused by the addition of EDTA-2Na dihydrate and specific amino acids as stabilizers.

FIG. 4 shows the osmolality variation of sugar solution caused by the addition of EDTA-2Na dihydrate and specific amino acids as stabilizers.

DETAILED DESCRIPTION

The present invention relates to a sugar infusion solution. According to the present invention, a sugar infusion solution capable of effectively enhancing the immune system and health is prepared by combining specific sugars among many sugars. The composition of the present invention comprises eight sugars, including glucose (Glu), galactose (Gal), mannose (Man), L-fucose (Fuc), xylose (Xy), N-acetylglucosamine (GlcNAc), N-acetylgalactosamine (GalNAc), and N-acetylneuraminic acid (NANA, also known as sialic acid).

These sugars are the main sugars that are indispensable for the synthesis of glycoproteins. It is known that sugar chains are attached to more than about 50% of proteins, and most of them exhibit specific functions of proteins only when sugars having specific structures bind thereto. In addition, bound sugar chains may increase or inhibit the functions of the proteins themselves, and thus play a role of more precisely regulating cell growth and immune activity.

For example, glucose acts as a representative energy source in the body, galactose functions as a differentiator between different species, and mannose has a glycemic control effect, immune activity and an anti-inflammatory effect. It is known that fucose attached to antibodies plays an important role in regulating the activity of antibody dependent cellular cytotoxicity (ADCC) and also plays a key role in bone growth. Xylose acts as an antifungal, antibacterial and anticancer agent that inhibits the binding of pathogens to the cell membrane mucus, and N-acetylglucosamine helps to produce cartilage. N-acetylgalactosamine functions to inhibit tumor cell growth, reduce rheumatoid arthritis, and inhibit aging, and N-acetylneuraminic acid has antiviral activity and plays a crucial role in brain growth.

Therefore, the above-described eight essential sugars can further enhance the immune system and health by direct injection as infusion solution.

Sugars other than glucose and galactose are more difficult to produce in the body as aging proceeds. Therefore, if the sugars are directly supplied through the present invention, they can effectively meet various physiological requirements such as cell growth and immune system enhancement. Thus, the composition of the present invention can act as comprehensive nutrition therapy. In addition, a complex of sugars and proteins has problems in that it is difficult to distribute throughout the body due to its high molecular weight even if injected into the body and that the complex itself injected into the body can act as an immunogen. However, since sugars themselves have relatively low molecular weights, they can be distributed throughout the body when injected into the body, and thus can provide more effective nutrition therapy.

However, the preparation of an infusion solution containing the above-mentioned sugar is very difficult because the sugars are easily denatured in an aqueous solution. In conventional injections or infusion solutions, stabilizers, chelating agents or the like were used to improve stability, but the results of an experiment conducted by the present inventors indicated that none of them stabilized an infusion solution containing the eight sugars.

The composition of the present invention comprises eight sugars, including glucose (Glu), galactose (Gal), mannose (Man), L-fucose (Fuc), xylose (Xy), N-acetylglucosamine (GlcNAc), N-acetylgalactosamine (GalNAc), and N-acetylneuraminic acid (NANA, also known as sialic acid).

According to the present invention, a stable sugar infusion solution has been developed by dissolving the above-described eight sugars with appropriate solubility. To dramatically improve the stability of sugar infusion solution, the present inventors have made efforts to prepare a stable sugar infusion solution using amino acids, because it is not known whether amino acids which are injectable into the human body while being safe can improve the stability of sugar infusion solution.

EXAMPLES

Hereinafter, the present invention will be described in detail with reference to examples to help understand the present invention. However, the following examples are merely to illustrate the present invention, but the scope of the present invention is not limited to the following examples. The examples of the present invention are provided to more completely explain the present invention to those skilled in the art.

Experimental Example 1. Preparation of Infusion Solution Containing Sugars and Stabilizers A. Materials and Devices Eight sugars, that is, glucose, galactose, mannose, L-fucose, xylose, N-acetylglucosamine, N-acetylgalactosamine, and N-acetylneuraminic acid, purchased from Sigma-Aldrich (Saint Louis, MO, USA), were used.

To adjust the pH of samples, 1N NaOH solution (Samchun Pure Chemical Co., Ltd.) was used.

As stabilizers, sodium bisulfite (Sigma-Aldrich) and more than 98% pure EDTA-2Na dehydrate (disodium edetate dihydrate, Daejung Chemicals & metals Co., Ltd.) were used.

Amino acids used to replace stabilizers in the present invention were more than 97% pure Sigma-Aldrich products, and the stabilizing effect of the amino acids was compared against the sample treated directly with the stabilizers.

The above-described components were used after dissolution in water for injection (JW Pharmaceutical Corp.), and pH and osmolality variations as time passed were measured using a PH meter (METTLER TOLEDO Seven Compact pH/Ion) and an osmolality meter (OSMOMAT 030, Cryoscopic osmometer).

B. Preparation of Sugar Mixture Solutions

As shown in Table 1 below, clear solution compositions F1~F6, each comprising a mixture of eight sugars, were prepared.

Specifically, the solubility until colorless and maximum solubility of each sugar were first examined.

Then, each sugar was added to 2 ml of water for injection, and stirred at room temperature until a clear solution was obtained. First, a sample was prepared by adding each sugar to 2 ml of water for injection in an amount corresponding to the solubility (colorless) of each sugar (F1). In addition, a sample was prepared by doubling the amount of sample F1, and the clearness of the solution was observed (F2).

From the next sample, the amount of each sugar in the previous sample was gradually increased or decreased (only galactose and glucose were added to samples F3 and F4), and at the same time, and the appropriate solubility of each sugar was examined until each sugar could be completely and clearly dissolved.

The pH and osmolality of each sample were measured using a pH meter and an osmolality meter.

The amount of each sugar added to each sample is shown in Table 1 below.

[Table 1] The solubility of each sugar and the composition of each sample

TABLE 1

The solubility of each sugar and the composition of each sample

Solubility and Composition of sugar powders

|   |   | Solubility [1] (Colorless) | Solubility [2] (Maximum) | (mg/ml) | | | | | |
|---|---|---|---|---|---|---|---|---|---|
|   |   |   |   | F1 | F2 | F3 | F4 | F5 | F6 |
| 1 | Galactose | 100 | 683 | 100 | 200 | 210 | 205 | 200 | 200 |
| 2 | Glucose | 133 | 909 | 135 | 270 | 280 | 276 | 270 | 270 |

TABLE 1-continued

The solubility of each sugar and the composition of each sample

Solubility and Composition of sugar powders

| | | Solubility [1] (Colorless) | Solubility [2] (Maximum) | F1 | F2 | F3 | F4 | F5 | F6 |
|---|---|---|---|---|---|---|---|---|---|
| 3 | Mannose | 50 | 500 | 50 | 100 | | | 110 | 100 |
| 4 | L-Fucose | 50 | 827 | 50 | 100 | | | 110 | 100 |
| 5 | N-Acetyl galactosamine | 50 | 100 | 50 | 100 | | | 110 | 100 |
| 6 | Xylose | 50 | 100 | 50 | 100 | | | 110 | 80 |
| 7 | N-Acetyl glucosamine | 50 | 50 | 50 | 100 | | | 110 | 100 |
| 8 | N-Acetyl neuraminic acid | 50 | 50 | 50 | 100 | | | 106 | 80 |

[1] Solubility (Colorless): Solubility until colorless
[2] Solubility (Maximum): A maximum of solubility
[3] Total volume: 2 mL C. Experimental Results The eight sugars were dissolved until the solution was as clear as possible, and as a result, the composition of F6, in which all the components were clearly dissolved, was determined to be most suitable.

The remaining six sugars (i.e., galactose, glucose, mannose, L-fucose, N-acetylgalactosamine, and N-acetylglucosamine) other than xylose and N-acetylneuraminic acid were still clearly dissolved even when they were added in an amount corresponding to two times the solubility until colorless described in the literature. However, when larger amounts were added, the solutions looked turbid while some suspended particles floated.

Xylose and N-acetylneuraminic acid were not clearly dissolved when added in an amount corresponding to two times the solubility until colorless. Thus, the two sugars (xylose and N-acetylneuraminic acid) were added in an amount of 80 mg/ml, which is slightly smaller than the amount corresponding to two times the solubility until colorless.

The initial pH of sugar solution sample F6 prepared by mixing all the eight sugars was 1.6, because an acidic sugar (N-acetylneuraminic acid) was included in the eight sugars.

Meanwhile, the osmolality of the sample was not even measured, presumably because the concentration of the solute was excessively high compared to that of the solvent. Thus, the sample was diluted with water for injection in order to the pH and osmolality of the sample to be close to the normal pH (venous blood: 7.36 to 7.4; arterial blood: 7.38 to 7.42) and normal osmolality (275 to 295 mOsm/l) of body fluids, and the pH was gradually increased using NaOH. In particular, the sample was diluted 10-fold by adding 1800 μl of water for injection to 200 μl of F6, and the pH was increased by the addition of 30 μl of NaOH, and as a result, a pH of 7.04 and an osmolality of 352 mOsm/l could be obtained, which are similar to the normal pH and normal osmolality of body fluids.

Therefore, in subsequent experiments, an appropriate amount of NaOH was added to the 10-fold diluted sugar solution of sample F6.

The experimental results are shown in Table 2 below.

[Table 2] pH and osmolality measurement results for a 10-fold dilution of sample F6

TABLE 2

Preparation of the solution diluted 10 times

| | No treatment | Diluted 10 times[1] | Diluted 10 times + NaOH[2] 20 μl | Diluted 10 times + NaOH 30 μ |
|---|---|---|---|---|
| pH | 1.6 | 2.38 | 3.18 | 7.04 |
| Osmolality (mOsm/l) | — | 355 | 354 | 352 |

[1] Diluted 10 times: F6 200 μl + Water for injection 1800 μl
[2] NaOH: 1 mol/L Sodium hydroxide solution (1N)

Experimental Example 2. Samples Containing Stabilizers

A. Addition of Stabilizers

Among additives for injections, each of sodium bisulfite and EDTA-2Na dihydrate, which are frequently used as stabilizers, was added to sample F6 prepared in Example 1-B, and variations in the color, pH and osmolality of the sample were observed and measured.

First, 200 μl of sample F6 was added to 1800 μl of water for injection, and then stirred at room temperature, thereby preparing six samples, each consisting of 2 ml of a 10-fold-diluted sugar solution (samples a, a-1, b, b-1, c and c-1).

Next, the pH of each of the six samples was measured, and then adjusted with NaOH so as to be close to in vivo plasma pH 7.4.

A 0.1% solution of sodium bisulfite was prepared by mixing 5 mg of sodium bisulfite as stabilizer with 5 ml of water for injection, and a 0.2% solution of EDTA-2Na dihydrate was prepared by mixing 10 mg of EDTA-2Na dihydrate with 5 ml of water for injection. Then, 110 μl of each of the prepared solutions was added to some of the six 10-fold-diluted sugar solutions.

Time-dependent variations in the color, pH and osmolality of the samples were observed in each case of whether the stabilizers (sodium bisulfite and EDTA-2Na dihydrate) were added or not and whether the samples were exposed to light or not.

The compositions of the six samples are shown in Table 3 below.

[Table 3] Samples a, a-1, b, b-1, c and c-1

TABLE 3

Samples a, a-1, b, b-1, c and c-1
Adding of sodium bisulfite(SB) and EDTA-2Na dihydrate for antioxidant effect experiments

| | antioxidant addition (SB or EDTA-2Na dihydrate) | light | initial pH | initial Osmolality (mOsmol/l) |
|---|---|---|---|---|
| a | X | O | 7.4 | 377 |
| a-1 | X | X | 7.52 | 397 |
| b | SB | O | 7.31 | 343 |
| b-1 | SB | X | 6.96 | 342 |
| c | EDTA-2Na dihydrate | O | 7.68 | 349 |
| c-1 | EDTA-2Na dihydrate | X | 7.54 | 343 |

B. Experimental Results

Undiluted initial sample F6 without any additives gradually turned yellow over time. This is because the added sugar components were oxidized gradually and decomposed into yellowish substances. For example, galactose is decomposed into 5-hydroxymethylfurfural (5-HMF) under acidic conditions, in which 5-HMF is yellow in color.

Thus, in order to prevent the changes in color, pH and osmolality caused by oxidation of the sample, the stabilizer sodium bisulfite or EDTA-2Na dihydrate was added to a solution obtained by 10-fold diluting sample F6 as described above, and then changes in the color, pH and osmolality of the sample were observed for 10 days.

The results are shown in Table 4 below.

[Table 4] Samples a, a-1, b, b-1, c and c-1

The pH variation of the samples (b and b-1) containing sodium bisulfite did not significantly differ from the pH variation of the samples (a and a-1) containing no stabilizer.

The osmolality variation of the samples containing sodium bisulfite was rather higher than the osmolality of the samples containing no stabilizer.

Similarly, the pH variation of the samples (c and c-1) containing EDTA-2Na dihydrate did not significantly differ from the pH variation of the samples containing no stabilizer.

Thus, it can be seen that sodium bisulfite and EDTA-2NA dihydrate are not suitable as stabilizers for sample F6.

However, when the pH and osmolality variations of the samples containing sodium bisulfite are compared with those of the samples containing EDTA-2Na dihydrate, it can be seen that the osmolality variation of the samples containing sodium bisulfite was lower than the osmolality variation of the samples containing sodium bisulfite.

Example 3. Preparation of Samples Containing Amino Acids

A. Preparation of Samples

The stabilization effect of addition of amino acids was tested. 2 ml of a sugar solution was prepared by 10-fold diluting the sample according to the dilution method of Example 1-(C).

Next, each of 17 amino acids was added to the sugar solution, and time-dependent changes in the color, pH and osmolality of each solution were measured.

Among 20 amino acids constituting proteins, cysteine and tryptophan were excluded because they showed an excessively high initial osmolality variation when added in a preliminary experiment, and tyrosine was excluded because it was hardly dissolved due to its excessively low solubility (0.45).

TABLE 4

Adding of sodium bisulfite (SB) and EDTA-2Na dihydrate for antioxidant effect experiments Samples a, a-1, b, b-1, c and c-1

| | antioxidant addition (SB or EDTA-2Na dihydrate) | light | initial pH | initial Osmolality (mOsmol/l) | color changes day0 | day2 | day6 | day10 | later pH day0 | day2 | day6 | day10 | variation | variation (%) |
|---|---|---|---|---|---|---|---|---|---|---|---|---|---|---|
| a | X | 0 | 7.4 | 377 | — | — | — | — | 7.4 | 5.4 | 4.7 | 4.44 | −2.96 | 40.00 |
| a-1 | X | X | 7.52 | 397 | — | — | — | — | 7.52 | 6.07 | 5.1 | 6.79 | −1.73 | 23.01 |
| b | SB | 0 | 7.31 | 343 | — | — | — | — | 7.31 | 7.2 | 6.1 | 5.24 | −2.07 | 28.32 |
| b-1 | SB | X | 6.96 | 342 | — | — | — | — | 6.96 | 4.58 | 4.46 | 4.22 | −2.74 | 39.37 |
| c | EDTA-2Na dihydrate | 0 | 7.58 | 349 | — | — | — | — | 7.68 | 7.25 | 7.06 | 4.94 | −2.74 | 36.68 |
| c-1 | EDTA-2Na dihydrate | X | 7.54 | 343 | — | — | — | — | 7.54 | 7.21 | 6.89 | 4.85 | −2.69 | 35.68 |

| | later Osmolality (mOsmol/l) | | | | | |
|---|---|---|---|---|---|---|
| | day0 | day2 | day6 | day10 | variation | variation (%) |
| a | 377 | 394 | 465 | 468 | 91 | 24.14 |
| a-1 | 397 | 267 | 376 | 396 | −2 | 0.60 |
| b | 343 | 367 | 454 | 460 | 117 | 34.11 |
| b-1 | 342 | 397 | 401 | 433 | 61 | 17.84 |
| c | 349 | 356 | 359 | 380 | 11 | 3.15 |
| c-1 | 343 | 346 | 348 | 350 | 7 | 2.04 |

As a result of the experiment, no color change was observed in all samples. That is to say, the color change pattern was not visually observed because the sugar solution itself was diluted 10-fold.

It can be seen that the amino acids added to the sample showing the lowest variations in color, pH and osmolality compared to the control containing the 10-fold-diluted sugar solution without containing amino acids have the best stabilization effect.

First, the pH of the 10-fold-diluted sugar solution was adjusted similar to the in vivo plasma pH by adding 30.8 µl of NaOH to 2 ml of the 10-fold-diluted sugar solution. However, to the samples wherein basic amino acids (L-lysine and L-arginine) were to be added, NaOH was not separately added because the amino acids themselves are basic in nature. Meanwhile, the addition of acidic amino acids may result in a rapid decrease in pH. Hence, in order to prevent this decrease in pH, acidic amino acids (L-aspartic acid and L-glutamic acid were added to the diluted sugar solution in an amount of 4 mg/ml, and neutral amino acids and basic amino acids were added to the diluted sugar solution in an amount of 10 mg/ml. Then, the time-dependent pH and osmolality of the diluted sugar solution was measured.

The composition of each sample is shown in Table 5 below.

[Table 5] Compositions of samples containing amino acids

Compositions of samples containing amino acids Adding of Amino acid for Antioxidant effect experiment

| | Amino acid | NaOH (µl) | Amino acid (mg/ml) | pH | Osmolality (mOsmol/l) |
|---|---|---|---|---|---|
| Control | X | | X | 7.26 | 381 |
| 1 | L-Methionine | | | 6.85 | 455 |
| 2 | L-Phenylalanine | | | 6.83 | 432 |
| 3 | L-Histidine | | | 7.37 | 430 |
| 4 | Glycine | | | 6.46 | 494 |
| 5 | L-Alanine | | | 6.88 | 486 |
| 6 | L-Valine | | | 6.85 | 469 |
| 7 | L-Leucine | 30.8 | 10 | 6.89 | 456 |
| 8 | L-Isoleucine | | | 6.67 | 464 |
| 9 | L-Proline | | | 7.17 | 470 |
| 10 | L-Serine | | | 6.72 | 473 |
| 11 | L-Threonine | | | 6.1 | 466 |
| 12 | L-Asparagine | | | 6.22 | 445 |
| 13 | L-Glutamine | | | 6.45 | 444 |
| 14 | L-Aspartic acid | | 4 | 3.25 | 406 |
| 15 | L-Glutamic acid | | | 3.59 | 405 |
| 16 | L-Lysine | X | 10 | 9.24 | 412 |
| 17 | L-Arginine | | | 9.36 | 408 |

B. Experimental Results

The stabilization effects of the amino acids added to the diluted sugar solution obtained by 10-fold diluting sample F6 were compared for 26 days, and as a result, the pH of a negative control containing no amino acid increased by pH, and the osmolality thereof increased by 3.67%.

In addition, in most of the samples, the pH after 26 days was slightly lower than the initial pH, and the osmolality after 26 days showed a tendency to increase. This appears to be a result of the decompositions of sugars and amino acids.

Samples showing a lower pH variation than the control were a total of 10 samples containing methionine, histidine, valine, isoleucine, serine, threonine, asparagine, glutamine, aspartic acid or glutamic acid, respectively, and samples showing a lower osmolality variation than the control were a total of 4 samples containing methionine, phenylalanine, histidine or aspartic acid, respectively.

Among these samples, the final pH variation of sample No. 14 containing aspartic acid was 0, indicating that the pH did not change for 26 days, and the osmolality variation thereof was also low. In addition, the final osmolality variation of sample No. 1 containing methionine was the lowest (0.44%), and the final pH variation thereof was also very low.

The experimental results are shown in Table 6 below and FIGS. 1 and 2.

[Table 6] Results of measurement of the pH and osmolality variations of samples containing amino acids

TABLE 6

Results of measurement of the pH and osmolality variations of samples containing amino acids Antioxidant effect of amino acids

| | Amino acid | NaOH (ul) | Amino acid (mg/ml) | pH | | | | | variaion | variaion (%) |
|---|---|---|---|---|---|---|---|---|---|---|
| | | | | day0 | day4 | day7 | day11 | day26 | | |
| Control | X | | X | 7.26 | 7.28 | 7.44 | 7.4 | 7.38 | 0.12 | 1.65 |
| 1 | L-Methionine | | | 6.85 | 6.78 | 6.81 | 6.85 | 6.83 | −0.02 | 0.29 |
| 2 | L-Phenyialanine | | | 6.83 | 6.68 | 6.69 | 6.71 | 6.68 | −0.15 | 2.20 |
| 3 | L-Histidne | | | 7.37 | 7.39 | 7.4 | 7.4 | 7.33 | −0.04 | 0.54 |
| 4 | Glycine | | | 6.46 | 6.37 | 6.41 | 6.43 | 6.33 | −0.13 | 2.01 |
| 5 | L-Alanine | | | 6.88 | 6.64 | 6.67 | 6.66 | 6.53 | −0.35 | 5.09 |
| 6 | L-Valine | | | 6.85 | 6.72 | 6.66 | 6.72 | 6.74 | −0.11 | 1.16 |
| 7 | L-Leucine | | 10 | 6.89 | 6.7 | 6.62 | 6.68 | 6.66 | −0.23 | 3.34 |
| 8 | L-Isoleucine | 30.8 | | 6.67 | 6.5 | 6.51 | 6.61 | 6.64 | −0.03 | 0.45 |
| 9 | L-Proline | | | 7.17 | 6.75 | 6.85 | 6.91 | 7.03 | −0.14 | 1.95 |
| 10 | L-Serine | | | 6.72 | 6.58 | 6.62 | 6.65 | 6.68 | −0.04 | 0.60 |
| 11 | L-Threonine | | | 6.1 | 6 | 6.01 | 6.05 | 6.08 | −0.02 | 0.33 |
| 12 | L-Asparagine | | | 6.22 | 6.12 | 6.14 | 6.19 | 6.27 | 0.05 | 0.80 |
| 13 | L-Glutamine | | | 6.45 | 6.39 | 6.38 | 6.4 | 6.42 | −0.03 | 0.47 |
| 14 | L-Aspartic acid | | 4 | 3.25 | 3.27 | 3.27 | 3.26 | 3.25 | 0 | 0.00 |
| 15 | L-Glutamic acid | | | 3.59 | 3.57 | 3.58 | 3.57 | 3.56 | −0.03 | 0.84 |
| 16 | L-Lysine | | | 9.24 | 9.1 | 9.06 | 9 | 8.97 | −0.27 | 2.92 |
| 17 | L-Arginine | X | 10 | 9.36 | 9.16 | 9.08 | 9.04 | 9.02 | −0.34 | 3.63 |

TABLE 6-continued

Results of measurement of the pH and osmolality variations of samples containing amino acids Antioxidant effect of amino acids

| | | Osmolality (mOsmol/l) | | | | | |
|---|---|---|---|---|---|---|---|
| | day0 | day4 | day7 | day11 | day26 | variaion | variaion (%) |
| Control | 381 | 381 | 383 | 386 | 395 | 14 | 3.67 |
| 1 | 455 | 455 | 450 | 448 | 453 | −2 | 0.44 |
| 2 | 432 | 434 | 430 | 428 | 427 | −5 | 1.16 |
| 3 | 430 | 434 | 435 | 433 | 438 | 8 | 1.86 |
| 4 | 494 | 495 | 492 | 489 | 535 | 41 | 8.30 |
| 5 | 486 | 488 | 484 | 481 | 524 | 38 | 7.82 |
| 6 | 469 | 473 | 466 | 465 | 514 | 45 | 9.59 |
| 7 | 456 | 456 | 447 | 445 | 486 | 30 | 6.58 |
| 8 | 464 | 473 | 462 | 457 | 500 | 36 | 7.76 |
| 9 | 470 | 482 | 469 | 465 | 561 | 91 | 19.36 |
| 10 | 473 | 479 | 476 | 469 | 521 | 48 | 10.15 |
| 11 | 466 | 475 | 467 | 463 | 538 | 72 | 15.45 |
| 12 | 445 | 447 | 439 | 438 | 482 | 37 | 8.31 |
| 13 | 444 | 458 | 441 | 444 | 483 | 39 | 8.78 |
| 14 | 403 | 406 | 403 | 402 | 406 | 3 | 0.74 |
| 15 | 405 | 411 | 406 | 405 | 494 | 89 | 21.98 |
| 16 | 412 | 412 | 408 | 408 | 457 | 45 | 10.92 |
| 17 | 408 | 402 | 400 | 399 | 449 | 41 | 10.05 |

Experimental Example 4. Compositions Containing Four Amino Acids as Stabilizers

Four amino acids (methionine, phenylalanine, histidine and aspartic acid) were selected, which showed low pH variations and low osmolality variations in Experimental Example 3. Compositions containing each of these amino acids as a stabilizer, a composition containing all the four amino acids, and a composition containing EDTA-2Na were prepared as shown in Table 9 below, and the pH and osmolality variations thereof were compared.

Specifically, methionine, phenylalanine, histidine or aspartic acid was added to the sugar solution obtained by 10-fold diluting sample F6, or all the four amino acids were added to the sugar solution, or EDTA-2Na dihydrate was added to the sugar solution, after which the pH and osmolality variations of the sugar solution were measured.

The results are shown in Table 7 below.

[Table 7] Experimental results

When aspartic acid was used as a stabilizer (sample No. 2), the pH variation was only 0.01, and the osmolality variation was 0, indicating that the osmolality did not change for 10 days.

Similarly, when the four amino acids were all used as stabilizers (sample No. 6), the pH variation was only 0.01, and the osmolality variation was also very low (0.52%).

In addition, the pH and osmolality variations of the above-described two samples were lower than those of sample No. 7 containing EDTA-2Na dihydrate as a stabilizer.

Experimental Example 5. Test for Long-Term Storage Stability

For each of the compositions used in Experimental Example 4 above, an accelerated test was performed from day 27, and the long-term storage stability for pH and osmolality variations of each composition were measured in comparison with the composition containing EDTA-2Na dihydrate (positive control).

TABLE 7

Experimental results

Antioxidant effect of amino acid and EDTA-2Na addition (room temperat

| | | amount | NaOH | pH | | | | Osmolality (mOsmol/l) | | | |
|---|---|---|---|---|---|---|---|---|---|---|---|
| | | | | before accelerated test | | variation | | before accelerated test | | variation | |
| | | (mg) | (ul) | day0 | day10 | variation | variation (%) | day0 | day10 | variation | variation (%) |
| 1 | Control | X | 40 | 10.25 | 9.98 | −0.27 | 2.63 | 356 | 358 | 2 | 0.56 |
| 2 | L-Aspartic acid | 8 | | 3.39 | 3.4 | 0.01 | 0.29 | 394 | 394 | 0 | 0.00 |
| 3 | L-Methionine | | | 8.28 | 8.04 | −0.24 | 2.90 | 388 | 390 | 2 | 0.52 |
| 4 | L-Phenylalanine | | | 8.62 | 8.23 | −0.39 | 4.52 | 382 | 385 | 3 | 0.79 |
| 5 | L-Histidne | | | 8.55 | 8.21 | −0.34 | 3.98 | 396 | 394 | −2 | −0.51 |
| 6 | 4 amino acids (Asp + Met + Phe + His) | 2 + 2 + 2 + 2 | | 6.29 | 6.3 | 0.01 | 0.16 | 384 | 386 | 2 | 0.52 |
| 7 | 0.4% EDTA-2Na | 8 | | 6.11 | 6.13 | 0.02 | 0.33 | 388 | 391 | 3 | 0.77 |

The accelerated test was performed at a temperature of 40±2° C. and a relative humidity of 75±5% for 46 days from day 27.

The experimental results are shown in Table 8 below and FIGS. 3 and 4.

[Table 8] Experimental results

TABLE 8

Experimental results

Antiocidant effect of amino acid and EDTA-2Na addition (room temperature)

| | | amount | NaOH | pH | | | | |
|---|---|---|---|---|---|---|---|---|
| | | | | before AT (accelerated test) | | | | |
| | | (mg) | (ul) | day0 | day10 | day14 | day18 | day26 |
| 1 | Control | X | 40 | 10.25 | 9.98 | 9.88 | 9.58 | 9.27 |
| 2 | L-Aspartic acid | 8 | | 3.39 | 3.4 | 3.41 | 3.42 | 3.4 |
| 3 | L-Methionine | | | 8.28 | 8.04 | 8.05 | 7.98 | 7.95 |
| 4 | L-Phenylalanine | | | 8.62 | 8.23 | 8.21 | 8.21 | 8.1 |
| 5 | L-Histidne | | | 8.55 | 8.21 | 8.17 | 8.17 | 8.09 |
| 6 | 4 amino acids (Asp + Met + Phe + His) | 2 + 2 + 2 + 2 | | 6.29 | 6.3 | 6.29 | 6.34 | 6.3 |
| 7 | 0.4% EDTA-2Na | 8 | | 6.11 | 6.13 | 6.14 | 6.12 | 6.08 |

| | | pH | | | | | | |
|---|---|---|---|---|---|---|---|---|
| | | after 6d of AT | after 12d of AT | after 25d of AT | after 35d of AT | after 46d of AT | variation | |
| | | day32 | day38 | day51 | day61 | day72 | variation | variation (%) |
| 1 | Control | 6.78 | 5.72 | 5.38 | 4.97 | 3.23 | −7.02 | 68.49 |
| 2 | L-Aspartic acid | 3.42 | 3.43 | 3.45 | 3.46 | 3.49 | 0.1 | 2.95 |
| 3 | L-Methionine | 7.32 | 6.6 | 5.84 | 5.21 | 4.11 | −4.17 | 50.36 |
| 4 | L-Phenylalanine | 7.15 | 6.16 | 5.55 | 4.87 | 3.68 | −4.94 | 57.31 |
| 5 | L-Histidne | 7.28 | 6.71 | 6.3 | 5.88 | 5.23 | −3.32 | 38.83 |
| 6 | 4 amino acids (Asp + Met + Phe + His) | 6.36 | 6.38 | 6.41 | 6.42 | 5.92 | −0.37 | 5.88 |
| 7 | 0.4% EDTA-2Na | 6.29 | 6.52 | 6.74 | 6.74 | 8.62 | 2.51 | 41.08 |

| | | Osmolality (m0smol/l) | | | | | | |
|---|---|---|---|---|---|---|---|---|
| | | before AT (accelerated test) | | | | | | |
| | | day0 | day10 | day14 | day18 | day26 | | |
| 1 | Control | X | 40 | 356 | 358 | 354 | 360 | 368 |
| 2 | L-Aspartic acid | 8 | | 394 | 394 | 392 | 395 | 391 |
| 3 | L-Methionine | | | 388 | 390 | 389 | 391 | 397 |
| 4 | L-Phenylalanine | | | 382 | 385 | 374 | 379 | 373 |
| 5 | L-Histidne | | | 396 | 394 | 387 | 399 | 395 |
| 6 | 4 amino acids (Asp + Met + Phe + His) | 2 + 2 + 2 + 2 | | 384 | 386 | 376 | 381 | 387 |
| 7 | 0.4% EDTA-2Na | 8 | | 388 | 391 | 400 | 386 | 393 |

| | | Osmolality (m0smol/l) | | | | | | |
|---|---|---|---|---|---|---|---|---|
| | | after 6d of AT | after 12d of AT | after 25d of AT | after 35d of AT | after 46d of AT | variation | |
| | | day32 | day38 | day51 | day61 | day72 | variation | variation (%) |
| 1 | Control | 392 | 482 | 498 | 521 | 702 | 346 | 97.19 |
| 2 | L-Aspartic acid | 404 | 415 | 436 | 441 | 461 | 67 | 17.01 |
| 3 | L-Methionine | 433 | 471 | 535 | 567 | 632 | 244 | 62.89 |
| 4 | L-Phenylalanine | 414 | 459 | 475 | 489 | 563 | 181 | 47.38 |
| 5 | L-Histidne | 457 | 460 | 484 | 498 | 546 | 150 | 37.88 |
| 6 | 4 amino acids (Asp + Met + Phe + His) | 392 | 410 | 455 | 482 | 512 | 128 | 33.33 |
| 7 | 0.4% EDTA-2Na | 430 | 539 | 632 | 711 | 711 | 516 | 132.99 |

As a result of 72 days of the long-term storage test including 46 days of the accelerated test, the pH variation of the composition containing all the four amino acids as stabilizers was only 0.37, but the pH variation of the composition containing EDTA-2Na dihydrate as a stabilizer was as high as 2.51. This corresponds to a difference in variation of about 7-fold when converted into percentage (%) (It corresponds to a difference in hydrogen ion concentration variation of about 140-fold when viewed in terms of hydrogen ion concentration). In addition, the osmolality variation of the composition containing all the four amino acids as stabilizers was only 128, but the osmolality variation of the composition containing EDTA-2Na dihydrate as a stabilizer was as high as 516. This corresponds to a difference in variation of about 4-fold when converted into percentage (%).

In addition, when aspartic acid was used as a stabilizer, the pH variation was 0.1, indicating that it was almost maintained, and the osmolality variation was also only 67. When converted into percentage (%), this pH variation corresponds to a difference of about 14-fold (It corresponds to a difference in hydrogen ion concentration variation of about 250-fold when viewed in terms of hydrogen ion concentration), and this osmolality variation corresponds a difference of about 8-fold.

Thus, it can be seen that when aspartic acid was used as a stabilizer or when methionine, phenylalanine, histidine and aspartic acid were used as stabilizers, the effect on long-term storage stability was greatly improved compared to when EDTA-2Na dihydrate was used.

Therefore, the use of aspartic acid as a stabilizer in an infusion solution requiring long-term storage stability can greatly improve the stability of the infusion solution.

INDUSTRIAL APPLICABILITY

The infusion solution composition according to the present invention has greatly improved stability, particularly, greatly improved long-term storage stability.

What is claimed is:

1. A method for promoting health, consisting of:
administering to a subject an intravenous injection comprising glucose, galactose, mannose, L-fucose, xylose, N-acetylglucosamine, N-acetylgalactosamine, N-acetylneuraminic acid, and a stabilizer, wherein the stabilizer is aspartic acid.

2. A method for promoting health, consisting of:
administering to a subject an intravenous injection comprising glucose, galactose, mannose, L-fucose, xylose, N-acetylglucosamine, N-acetylgalactosamine, and N-acetylneuraminic acid,
wherein the intravenous injection comprises methionine, phenylalanine, histidine, and aspartic acid as stabilizers.

* * * * *